(12) United States Patent
Cailleteau (10) Patent No.: US 10,765,578 B2
(45) Date of Patent: Sep. 8, 2020

(54) ARTICLE FOR COLLECTING THE URINE AND STOOLS OF A USER

(71) Applicant: SWISS SAFE COLLECT SA, Neuchatel (CH)

(72) Inventor: Benoit Cailleteau, Blonay (CH)

(73) Assignee: SWISS SAFE COLLECT SA, Neuchatel (CH)

( * ) Notice: Subject to any disclaimer, the term of this patent is extended or adjusted under 35 U.S.C. 154(b) by 545 days.

(21) Appl. No.: 15/510,927

(22) PCT Filed: Sep. 15, 2015

(86) PCT No.: PCT/EP2015/071025
§ 371 (c)(1),
(2) Date: Mar. 13, 2017

(87) PCT Pub. No.: WO2016/041927
PCT Pub. Date: Mar. 24, 2016

(65) Prior Publication Data
US 2017/0273843 A1    Sep. 28, 2017

(30) Foreign Application Priority Data
Sep. 15, 2014   (FR) ..................... 14 58658

(51) Int. Cl.
*A61G 9/00*   (2006.01)
*A61B 10/00*  (2006.01)
(Continued)

(52) U.S. Cl.
CPC ............ *A61G 9/003* (2013.01); *A61B 10/007* (2013.01); *A61G 7/05769* (2013.01); *A47K 13/08* (2013.01)

(58) Field of Classification Search
CPC combination set(s) only.
See application file for complete search history.

(56) References Cited

U.S. PATENT DOCUMENTS 5,394,571 A * 3/1995 Vernon .................. A61G 9/003
                                                    4/450
5,619,757 A * 4/1997 Baratta .................. A47K 13/06
                                                    4/239
(Continued)

FOREIGN PATENT DOCUMENTS

CN    2863062 Y    1/2007
EP    0658 337 A1  6/1995
(Continued)

OTHER PUBLICATIONS

PCT International Search Report, PCT/EP2015/071025, dated Sep. 15, 2015, Priority Date Sep. 15, 2014, Damya Mammeri, Nov. 23, 2015, 4 pages.

*Primary Examiner* — Tatyana Zalukaeva
*Assistant Examiner* — Guy K Townsend
(74) *Attorney, Agent, or Firm* — Fay Sharpe LLP; James E. Scarbrough (57) ABSTRACT

An article (1; 100) for collecting urine (300) and stools (400) of a user, the article having a support surface (10A) for supporting the buttocks of the user; and a chamber (20) that communicates with an opening (10E) defined by the support surface (10A) and that presents a bottom portion (22); and a spacer (10) suitable for maintaining the bottom portion at a distance from the support surface. The article has an internal wall element (23; 123) that is situated at a position vertically intermediate between the support surface (10A) and the bottom portion (22) and that is suitable for adopting a first configuration and a second configuration. In the first configuration, the internal wall element forms an obstacle for substantially preventing stools (400) from passing to the bottom while allowing communication for urine (300). In the second configuration, the obstacle is substantially elimi- (Continued)

nated so as to allow stools to pass to the bottom of the chamber (20).

14 Claims, 3 Drawing Sheets

(51) Int. Cl.
*A61G 7/057* (2006.01)
*A47K 13/08* (2006.01)

(56) References Cited

U.S. PATENT DOCUMENTS

| | | | | |
|---|---|---|---|---|
| 5,876,393 | A * | 3/1999 | Ahr | A61F 13/49009 |
| | | | | 604/367 |
| 5,997,520 | A | 12/1999 | Ahr et al. | |
| 6,324,705 | B1 * | 12/2001 | Zephier | A47K 17/02 |
| | | | | 4/254 |
| 6,449,782 | B1 * | 9/2002 | Jones | A47K 11/02 |
| | | | | 4/451 |
| 6,783,826 | B2 * | 8/2004 | Sherrod | A47K 11/105 |
| | | | | 4/245.6 |
| 8,312,573 | B2 * | 11/2012 | Ron | A47K 11/045 |
| | | | | 4/479 |
| 8,453,274 | B1 * | 6/2013 | Olmstead | A61G 9/003 |
| | | | | 4/456 |
| D847,978 | S * | 5/2019 | Gabrielson | A61G 9/003 |
| | | | | D24/123 |
| 2002/0004949 | A1 * | 1/2002 | Spitzer | A61G 9/003 |
| | | | | 4/451 |
| 2003/0116575 | A1 * | 6/2003 | Ellingson | A61G 9/003 |
| | | | | 220/719 |
| 2003/0181880 | A1 * | 9/2003 | Schwartz | A61G 5/1054 |
| | | | | 604/358 |
| 2005/0000008 | A1 * | 1/2005 | Spitzer | A61G 9/003 |
| | | | | 4/483 |
| 2005/0182382 | A1 * | 8/2005 | Bailey | A61F 13/495 |
| | | | | 604/385.101 |
| 2015/0182405 | A1 * | 7/2015 | Gradov | A61G 9/003 |
| | | | | 4/452 |
| 2017/0273843 | A1 * | 9/2017 | Cailleteau | A61G 7/05769 |

FOREIGN PATENT DOCUMENTS

| | | |
|---|---|---|
| EP | 0 705 087 A1 | 7/1998 |
| EP | 0762 861 A1 | 2/2000 |
| EP | 0762 862 A1 | 9/2000 |
| EP | 1 582 185 A1 | 5/2005 |
| EP | 1 265 574 A2 | 3/2006 |
| JP | 59034048 A | 2/1984 |
| WO | WO1995/00089 | 1/1995 |
| WO | WO2001/050995 | 7/2001 |
| WO | WO2001/050997 | 7/2001 |
| WO | WO 2001/93738 A1 | 12/2001 |

* cited by examiner

ARTICLE FOR COLLECTING THE URINE AND STOOLS OF A USER

BACKGROUND OF THE INVENTION

The present invention relates to an article for collecting urine and stools of a user, more particularly a bedridden user, whether an adult or a child, and whether female or male.

Usually, in order to collect urine and stools from a bedridden patient (in particular in a hospital or in a retirement home) who is not capable of using the toilet, use is made either of disposable diapers or else of washable bedpans.

None of those known solutions is satisfactory from a hygiene point of view.

When a diaper is used, it needs to be removed from the patient's body in order to be disposed of and replaced by another diaper that is clean. There is a risk of accidental contact between the patient's fecal matter and the person (e.g. a nurse) changing the diaper, or between the fecal matter and any other equipment, or the ground.

When using a bedpan, since it is not disposable, it needs to be cleaned in order to be reused. That means that each time the bedpan is soiled, a person (e.g. a nurse) needs to intervene to remove the soiled bedpan, replace it with another bedpan that is clean, and then transport the soiled bedpan to a facility where it can be cleaned and then disinfected. Consequently, bedpans are handled very many times. Furthermore, the cleaning and disinfection of bedpans can be imperfect, and an imperfectly disinfected bedpan can thus be put into contact with another patient, another person, other equipment, or the ground.

However it is now known that repeated contact with fecal matter, or with a surface or equipment contaminated therewith, increases the risk of contamination by various microorganisms contained in fecal matter, and in particular bacteria. This is particularly problematic in an establishment such as a hospital or a retirement home where nosocomial infections and in particular infections by bacteria that are multiply resistant to antibiotics, represent a health risk for patients, and also for care staff.

There thus exists a need for a device for collecting urine and stools of a user that makes it possible to limit or avoid accidental contact between a user's fecal matter and the person handling the device.

In this respect, a disposable container suitable for fitting to a conventional bedpan is proposed in Document US 2003/0116575. That disposable container has a bottom storage compartment for storing the patient's urine and stools, and a top reception compartment for directing urine and stools from the patient to the storage compartment. The reception compartment and the storage compartment are separated from each other by an antisplash element comprising at least one flexible flap. The at least one flexible flap defines a slot that opens to pass urine and stools from the patient, and then closes again once they have passed through the stools.

Nevertheless, the disposable container proposed in Document US 2003/0116575 does not enable stools to be separated from urine, even temporarily, thereby increasing in particular the risk of the patient being soiled. Furthermore, Document US 2003/0116575 does not propose a solution for limiting or preventing bedsores appearing when the user needs to be bedridden for a long duration.

OBJECT AND SUMMARY OF THE INVENTION

To remedy the above drawbacks, the present invention proposes an article for collecting urine and stools of a user, the article comprising: a support surface for supporting the buttocks of the user; and a chamber that communicates with an opening defined by the support surface and that presents a bottom portion; and spacer means suitable for maintaining the bottom portion at a distance from the support surface; wherein the chamber has an internal wall element that is situated at a position vertically intermediate between the support surface and the bottom portion and that is suitable for adopting a first configuration and a second configuration. In the first configuration, the internal wall element subdivides the chamber into a top compartment and a bottom compartment, forming an obstacle between these compartments that is for retaining stools in the top compartment while putting the compartments into communication for urine. In the second configuration of the internal wall element, the obstacle is substantially eliminated so as to allow stools to pass into the bottom of the chamber.

With the above-described article, since the internal wall element is situated at a position that is vertically intermediate between the support surface and the bottom portion, when the internal wall element is in its first configuration, the top compartment possesses an inside volume suitable for receiving stools from the user installed on the article, who can thus urinate and defecate into the article without soiling other equipment, such as a bed.

Furthermore, when the internal wall element is in its first configuration, urine passes directly into the bottom compartment, while stools are retained by the obstacle in the top compartment so long as the internal wall element remains in its first configuration. Thus, stools are not diluted in urine, thereby limiting the risk of the soiling the user, specifically since the article generally remains in contact with the user for a certain amount of time, on a seat or in a bed, given that the article of the invention is used more particularly for patients who are sitting or bedridden.

Thereafter, when it is desired to replace the soiled article by another article that is clean, the person in charge of replacing the article causes the internal wall element to pass from its first configuration to its second configuration. In the second configuration of the internal wall element, the obstacle formed by the internal wall element is substantially eliminated, i.e. the internal wall element remains inside the chamber but its shape is modified so that it substantially no longer constitutes an obstacle to passing stools. The stools thus pass into the bottom compartment where they are trapped. In this way, the stools are moved further away from the user and from the person replacing the article. Thus, the risk of contact with fecal matter is eliminated or greatly limited.

In a possibility, the internal wall element comprises at least one portion of flexible film.

It is thus easy to constitute at least a portion of the internal wall element by securing one or more portions of flexible film to the wall of the chamber.

In a possibility, the obstacle is formed by at least one reentrant fold in at least one portion of flexible film.

It is thus particularly easy to eliminate the obstacle on passing from the first configuration to the second, since this elimination can be achieved merely by unfolding at least one fold. Furthermore, the fold locally reinforces the portion of flexible film that, in the first configuration, remains well positioned, avoiding untimely elimination of the obstacle, the folded portion forming effective separation between the two compartments and forming an effective support for stools, while in the first configuration.

In a possibility, in the first configuration, communication between the compartments comprises an opening that is substantially slot-shaped, the slot being defined by two reentrant folds in two portions of flexible film placed facing each other, and the obstacle being formed by the two reentrant folds.

These folds present the above-mentioned advantages. Furthermore, on passing from the first configuration to the second configuration, the obstacle is eliminated while widening the slot. Furthermore, the internal wall element is relatively simple to construct since it suffices to secure each of the two portions of flexible film with a wall of the chamber.

The slot may lie substantially in the longitudinal direction of the article, or substantially in the transverse direction of the article.

In a possibility, in the first configuration, the width of the slot lies in the range 0.5 centimeters (cm) to 3 cm.

This width is then sufficient to pass urine, while substantially retaining the user's stools.

In a possibility, the length of the slot lies in that range 10 cm to 60 cm.

This length is then sufficient to pass almost all of the user's stools on passing from the first configuration to the second configuration.

In a possibility, the bottom portion and the at least one portion of flexible film are formed out of the same piece of flexible film.

This simplifies construction of the article.

In a possibility, the at least one portion of flexible film is connected at its top end to the support surface and at its bottom end to the bottom portion.

Thus, for causing the internal wall element to pass from its first configuration to its second configuration, it suffices to take hold of the portion of the article carrying the support surface and to pull this portion upwards, thereby automatically causing the at least one reentrant fold to unfold. Handling of the article is thus simplified, and if the article is handled correctly, the risk of accidental contact between the person in charge of handling the article and the patient's stools is very limited.

In a possibility, a portion of the chamber extends under the support surface.

The capacity of the compartment is thus increases.

In a possibility, an absorbent element is placed on the bottom portion.

This limits the risk of urine spilling when the article is accidentally turned over, or when the bottom is punctured, or when the wall element is damaged. Furthermore, the risk of splashing when spools pass suddenly from the top compartment to the bottom compartment is avoided or eliminated, even when the bottom compartment has previously collected a large quantity of urine.

In a possibility, the spacer means comprise an inflatable tube.

It is thus possible to keep the bottom portion at a distance from the support surface using means that are simple to use.

In a possibility, the support surface is the top surface of an inflatable tube.

In this way, the user's buttocks are supported by the inflatable portion. The article can then serve not only to collect urine and stools of a bedridden user, but also to limit or prevent the appearance of bed sores when the user needs to be bedridden for a long duration.

In a possibility, the inflatable tube includes an inflation valve having a check valve.

The inflatable tube can thus be inflated by delivering external air under pressure, without deflating in undesirable manner.

In a possibility, the long dimension of the opening defined by the support surface is not less than 20 cm.

The size of the opening is then sufficient to substantially surround the user's genital region, thereby avoiding other equipment, such as a bed, being soiled by urine or by stools.

BRIEF DESCRIPTION OF THE DRAWINGS

The invention can be well understood and its advantages appear better on reading the following detailed description of embodiments given as non-limiting examples. The description refers to the accompanying drawings, in which.

DETAILED DESCRIPTION OF THE INVENTION

In all of the figures and in the following description, Dv, Dl, and Dt specify respectively the vertical, longitudinal, and transverse directions of the article of the invention.

The vertical direction Dv is the direction perpendicular to the surface on which the article is installed (e.g. the surface of a bed). The longitudinal direction Dl of the article is the direction that coincides with the head-torso-legs axis of a user when installed on the article.

The transverse direction Dt is the direction in a horizontal plane that is perpendicular to the longitudinal direction Dl.

First Embodiment

Figure 1:
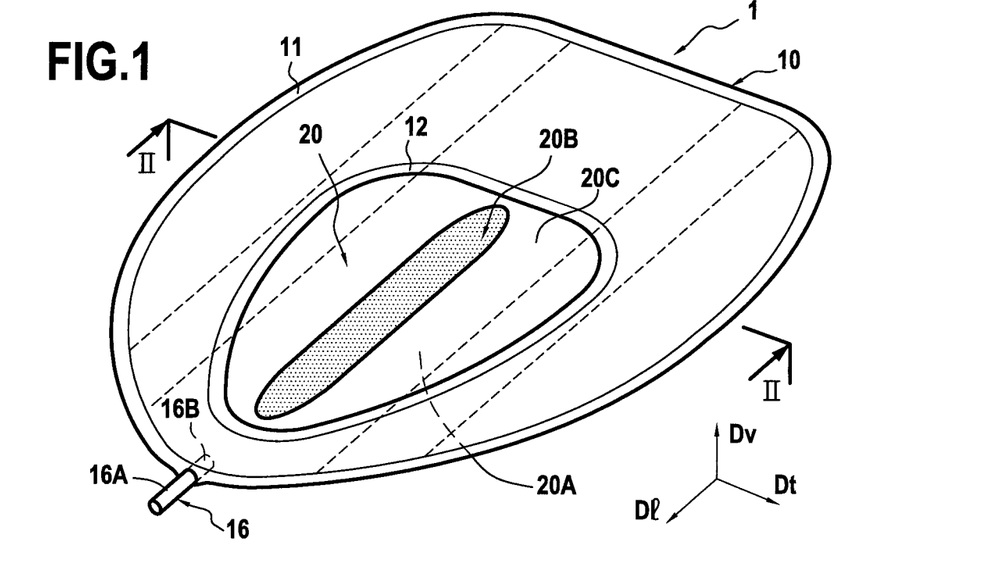
FIG. 1 is a perspective view from above of an article in a first embodiment of the invention.

As can be seen in FIG. 1, an article 1 in a first embodiment comprises an inflatable tube 10 defining an opening 20B.

The inflatable tube 10 is made by connecting together two films cut out to the appropriate dimensions and shapes (in particular a ring shape) so as to obtain an outer connection edge 11 and an inner connection edge 12. For example, the films are thin films of plastics material (e.g. of polyethylene (PE)) that are unrolled continuously, with the connection between them being made by locally melting the plastics material, in well-known manner. The plastics material may also be a bioplastic, in particular a plastic that is biodegradable, or indeed compostable, e.g. based on corn (maize) starch. Naturally, the films could also be connected together by means other than locally melting the plastics material, e.g. by adhesive.

The inflatable tube 10 presents a top surface 10A that serves as a support surface for a user's body, as described in greater detail below, and a bottom surface 10B. The top surface 10A defines an opening 10E in its center.

The inflatable tube 10 presents an inflation valve 16 with an admission pipe 16A and a check valve 16B. The inflation valve 16 may be positioned anywhere on the inflatable tube 10.

As described in greater detail below, the inflation valve 16 is used to inflate the inflatable tube 10 prior to installing the article 1 under a user. The inflatable tube 10 may be inflated by any means, including a person blowing into it like blowing up a party balloon. Nevertheless, it is also possible to use an external pump, a pump installed on the article 1 (not shown), or medical oxygen or air under pressure when available in an establishment such as a hospital or a retirement home. Once the inflatable tube 10 has been inflated, or while it is being inflated, the check valve 16B serves to prevent it deflating. Check valves suitable for this purpose are known and are not described in detail herein.

It should be observed that in addition to or as a replacement for inflation using external oxygen or air, it is also possible to arrange for the inflatable tube 10 to contain an appropriate quantity of chemical compounds that possess the property of producing gas when they are put into contact, and to provide a system for putting them into contact, e.g. by breaking an internal wall that initially keeps the compounds apart.

Figure 2:
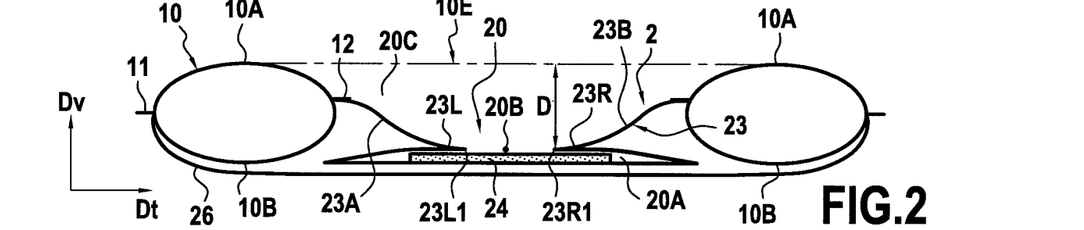
FIG. 2 is a section view on II-II of the article shown in FIG. 1.

As can be seen in the section view of FIG. 2, the article 1 presents a chamber 20 with an internal wall element 23.

The internal wall element 23 is situated in a position that is vertically intermediate between the support surface 10A and the bottom 22 of the article 1. In other words, when the article 1 is placed horizontally on a surface, the internal wall element 23 is situated lower than the support surface 10A and higher than the bottom 22. Insofar as it is flexible, the internal wall element 23 may nevertheless tend to sag under its own weight and touch the bottom.

FIG. 2 shows the article 1 when the internal wall element 23 is in the configuration that it adopts when the inflatable tube 10 is inflated and the article 1 is placed at rest on a horizontal surface (referred to below as the "first" configuration).

In this first configuration, the internal wall element 23 subdivides the chamber 20 into a top compartment 20C and a bottom compartment 20A.

The top compartment 20C communicates upwards with the outside through the opening 10E, and it is defined laterally by the inner edges of the inflatable tube 10.

Figure 3A:
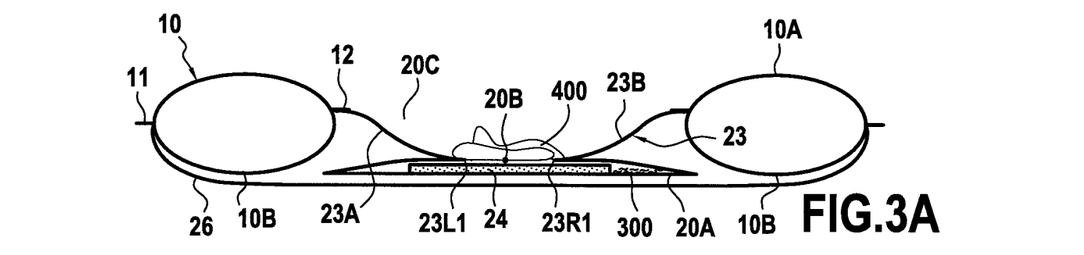
FIGS. 3A and 3B are section views on II-II of the article shown in FIG. 1, while it is in use.

Since the internal wall element 23 is situated lower down than the support surface 10A, it can be understood that the top compartment 20C possesses vertical dimensions and an inside volume enabling it to receive stools 400 of the user (see FIG. 3A). Preferably, the height of the internal wall element 23 is selected in such a manner that when the user has defecated, the stools 400 are kept at a distance from the user's skin. For example, the distance D between the internal wall element and the plane defined by the support surface may be of the order of 3 cm to 10 cm.

The bottom compartment 20A is situated under the top compartment 20C and communicates therewith via an opening 20B defined by the internal wall element 23. The bottom of the bottom compartment 20A coincides with the bottom 22 of the article 1.

In general manner, the vertical dimensions of the bottom compartment 20A are small (in FIGS. 2 and 3A they are exaggerated for reasons of clarity), and its top wall, defined specifically by the bottom face of the internal wall element, may even come into contact with the bottom 22, but without that impeding the operation of the article 1. Nevertheless, it is desirable for the bottom compartment 20A to be capable of containing the user's urine 300. For this purpose, in the example shown, the bottom 22 of the compartment is lined with an absorbent element 24 that is capable of absorbing urine, at the cost of swelling a little in volume. The absorbent element 24 may be of the type conventionally used in absorbent diapers for children or adults. It may be fastened (e.g. by adhesive) on the bottom portion 22, or it may merely by placed on the bottom portion 22.

Although not shown in the figures, if it is desired to increase the capacity of the bottom compartment 20A, it is possible to enlarge it in the transverse direction Dt so that it extends in part to beneath the top surface 10A.

In the first configuration (see FIG. 3A), the internal wall element 23 forms an obstacle to passing the user's stools 400. The term "forms an obstacle" is used to mean that the internal wall element 23 tends to retain the stools 400, preventing or limiting their passage towards the bottom of the chamber 20, and consequently the stools 400 are held essentially at a distance from the bottom portion 22 without being left in contact with the urine contained in the bottom compartment 20A.

Provision is also made for the internal wall element to be capable of responding to external handling by adopting a configuration that is different from the first configuration (which configuration is referred to below as the "second" configuration).

In the second configuration, the obstacle formed by the internal wall element 23 is substantially eliminated, i.e. the internal wall element 23 remains inside the chamber 20, but its shape is modified in such a manner that it substantially no longer forms an obstacle to passing stools 400 (e.g. because the opening 20B has become larger). The stools 400 then pass under gravity towards the bottom of the chamber 20. Thus, the stools 400 and the urine 300 are to be found together in the bottom of the chamber 20 and at a distance from the opening 10E, from the support surface 10A, and from the skin of the user, such that the risk of contact between the stools 400 and the skin of the person handling the article in its second configuration are limited.

Optionally, the article 1 may have an external wall 26, e.g. a flexible film of polyethylene (PE) or of biodegradable plastics material, which wall is connected to the outer connection edge 11, encompassing the internal wall element 23 and covering the bottom portion 22, i.e. if the bottom portion 22 is accidentally damaged, any urine or stools escaping therefrom will be trapped by the external wall 26.

There follows a description of the use and the operation of the article 1.

In order to install the article 1 between a surface, e.g. the surface of a bed on which a user is bedridden, and the user's body, the inflatable tube 10 is inflated as described above, and then the user is installed so that the buttocks are supported by the support surface 10A. Thus, when the user is bedridden, the inflatable tube 10 supports the user, thereby limiting or preventing the appearance of bed sores. It should be observed that when the user is installed, the internal wall element 23 is in the above-mentioned first configuration.

Figure 4A:
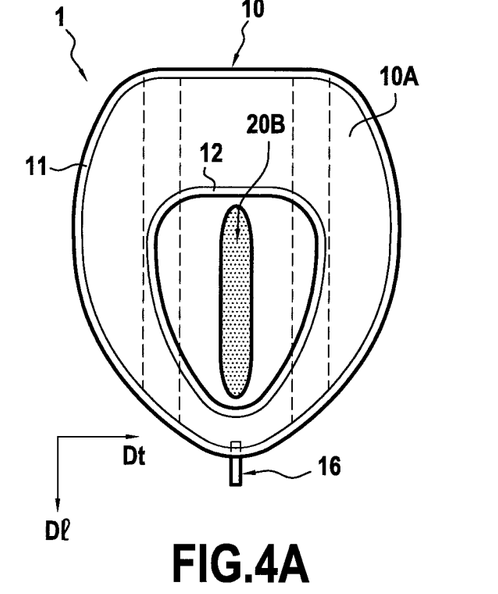
FIG. 4A is a plan view of the article shown in FIG. 1.
Figure 4B:
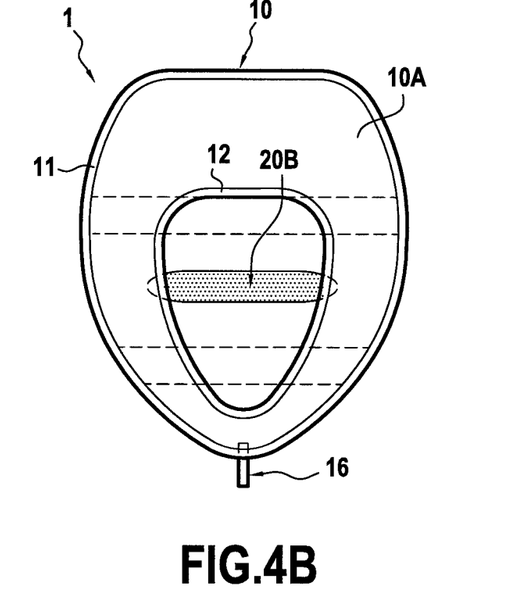
FIG. 4B is a view analogous to FIG. 4A, for a variant embodiment.

As can be seen in FIGS. 1, 4A, and 4B, the outline of the inflatable tube 10 is preferably generally ellipsoid in shape (i.e. it has a shape analogous to the outline of an egg), such that its long dimension coincides with the longitudinal direction Dl, its short dimension coincides with the transverse direction Dt, and its outline is wider in the region of the inflatable tube 10 that is closer to the user's torso (the top of FIGS. 4A and 4B). This improves the support provided for the user.

In order to further improve the support provided for the user, it is also possible to make provision for the tube to be wider and/or thicker in its region close to the user's back (at the top of FIGS. 4A and 4B). Nevertheless, it is possible to envisage other shapes for the inflatable tube 10, should that be necessary.

In any event, the user is installed in such a manner that the user's head-torso-legs axis coincides substantially with the longitudinal direction Dl, and the genital region is above the opening 10E of the inflatable tube and the opening 20B.

In summary, the article 1 is generally in the shape of a preferably ellipsoid swim ring to which a chamber 20 has been added to receive urine and stools, and the user is prone so that the user's genital region overlies the central opening of the ring.

After the user has urinated and/or defecated, it is necessary to replace the article 1.

When the internal wall element 23 is in the first configuration, it forms an obstacle to passing stools 400. As explained above, the stools 400 are thus held at a distance from the user's skin. Furthermore, since the opening 20B is not closed, it provides communication through which urine 300 can pass into the bottom compartment 20A.

By externally manipulating the article 1, the internal wall element 23 is caused to pass from the first configuration to the second configuration. Thus, the obstacle formed by the internal wall element 23 substantially disappears, thereby allowing the stools 400 to pass into the bottom compartment 20A.

If an absorbent element 24 is placed in the bottom portion 22, most or all of the urine 300 is absorbed by the absorbent element 24. This avoids or eliminates any risk of splashing in the event of the stools 400 passing too quickly into the bottom compartment 20A, assuming that it has previously received a large quantity of urine 300. This avoids urine spilling when the article is accidentally overturned, or when the bottom portion 22 is pierced, or more generally when the flexible film 23 is damaged. These last two points are particularly desirable when, for reasons of economy, it is decided not to cover the flexible film 23 with the external wall 26, as described above.

When the internal wall element 23 is in its second configuration, the soiled article 1 can be transported to another location, and it can be replaced with a new article 1 that is clean.

In general manner, it is envisaged that the article 1 is for single use and that it is disposable. This means that the article 1 is designed to be disposed of directly after use, e.g. by incineration. In this respect, making the article 1 out of flexible films of polyethylene (PE) or of bioplastic is advantageous, since the article 1 is thus of sufficiently low cost for that to be economically viable. Furthermore, if the article 1 is disposable, there is no longer any need to provide a facility for cleaning soiled articles, as is presently necessary with known bedpans, nor is there any need to move these articles around an establishment. This avoids increasing the number of contacts between these articles and other equipment or surfaces.

Specifically, in order to dispose of the article 1, the inflatable tube 10 is deflated, e.g. by tearing the inflatable tube 10 along a line of weakness (not shown), or indeed by puncturing it with a sharp object, and it is then placed in an appropriate container. If circumstances require it, the container may be a container for receiving medical wastes.

There follows a description in greater detail of a possible configuration of the internal wall element 23.

The internal wall element 23 may comprise at least one portion of flexible film that is suitable for being connected at its top end to the support surface (more precisely to the inflatable tube 10), and at its bottom end to the bottom portion 22. It can be seen that said at least one portion of the flexible film and the bottom portion may be made from a single piece of film that is folded appropriately.

For example, the top end of the at least one portion of flexible film may be connected to the inner connection edge 12, or more generally to the bottom surface 10B of the inflatable tube 10. There is no need for the flexible film portions to be connected to the inflatable tube 10 in symmetrical manner. In other words, the top ends of the flexible film portions may be connected to the inflatable tube 10 at different heights from one another.

In this embodiment, the opening 20B is closed (e.g. by local welding) at its ends close to the vicinity of the inner connection edge 12 (see FIGS. 4A and 4B).

The at least one portion of flexible film is shaped in such a manner that, in the first configuration, it forms at least one reentrant fold so that the obstacle for passing stools 400 is formed by this at least one reentrant fold. In the meaning of the present description, the fact that the fold is "reentrant" means that the fold hinge (given references 23L1 and 23R1 in FIG. 2) is situated further towards the inside of the article when seen in section on the transverse direction Dt than the two flanks of the fold that are connected together by the hinge. In other words, the shape of the fold tends to project at least one portion of flexible film towards the inside of the chamber 20.

Like the inflatable tube 10, the at least one portion of flexible film may be made of a flexible film of polyethylene (PE) or of biodegradable plastics material. Preferably, the at least one portion of flexible film is of thickness that is sufficient to support the weight of stools 400 without being torn or damaged, but thin enough to enable it to fold and unfold easily. For example, this thickness may lie in the range 20 micrometers (μm) to 500 μm, and preferably in the range 30 μm to 100 μm.

Figure 3B:
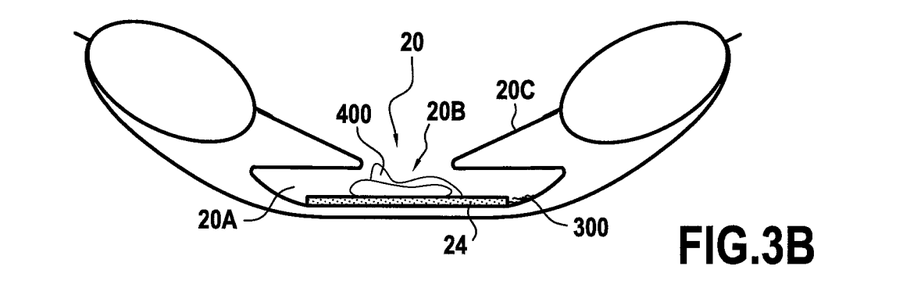

FIGS. 2, 3A, and 3B show an example configuration in which the article 1 has two flexible film portions 23A and 23B placed facing each other. Each flexible film portion 23A and 23B includes a respective reentrant fold, which folds are given respective references 23L and 23R. The hinges 23L1 and 23R1 of these reentrant folds define the opening 20B, which is then substantially in the shape of a slot.

As can be seen in FIGS. 4A and 4B, the slot may be substantially aligned with the longitudinal direction Dl, or substantially aligned with the transverse direction Dt. The article 1 operates identically in both situations.

In order to enable practically all of the user's stools to pass through when passing from the first configuration to the second configuration, as described below, the slot may have a length lying in the range 10 cm to 60 cm. Nevertheless, in this embodiment, it is preferable for the length of the slot to lie in the range 10 cm to 40 cm.

Preferably, in order to ensure that the size of the opening 10E is then sufficient to substantially surround the user's genital region, so as to avoid other materials such as a bed being soiled by urine or stools, the opening 20E is selected so that its long dimension is not less than 20 cm.

In the first configuration of the internal wall element 23, as shown in FIG. 3A, the reentrant folds 23L and 23R form an obstacle to passing stools 400. Nevertheless, since the slot 20B defined by the hinges 23L1 and 23R1 of the reentrant folds 23L and 23R is not closed, it provides communication through which urine 400 can pass into the bottom compartment 20A.

For example, in order to provide communication that enables urine 300 to pass without allowing stools 400 to pass, the slot 20B may have a width lying in the range 0.5 cm to 3 cm.

In order to cause the internal wall element 23 to pass from its first configuration (FIG. 3A) to its second configuration (FIG. 3B), it suffices to take hold of the inflatable tube 10 at two distinct points (that are preferably substantially diametrically opposite), preferably situated on its outer periphery, and to raise it upwards in the vertical direction Dv. Since the flexible film portions 23A and 23B are fastened to the bottom surface 10B of the inflatable tube 10, or to the bottom connection edge 12, the reentrant folds 23L and 23R "unfold" progressively as the inflatable tube 10 is pulled upwards. It should be observed that it is preferable to take hold of the inflatable tube 10 in a direction that is perpendicular to the axis of the slot (i.e. the line between the two points where the tube is held is substantially perpendicular to the axis of the slot), so as to avoid impeding unfolding of the flexible film 23A.

When the reentrant folds 23L and 23R "unfold", the slot 20B widens progressively. Thus, the obstacle formed by the reentrant folds 23L and 23R disappears substantially, thereby enabling the stools 400 to pass into the bottom compartment 20A.

Although the above-described article presents a reentrant fold on both sides of a substantially slot-shaped opening, it is also possible to provide an opening of a shape that is different (triangular, quadrangular, etc.) with a portion of flexible film presenting a reentrant fold for each side of the opening, or indeed configurations in which one or more sides of the opening present two or more superposed folds.

It can thus be understood that if the article 1 is handled correctly, the risk of accidental contact between the stools 400 and the person replacing the article 1 is very low. Specifically, since the person needs only take hold of two points of the inflatable tube 10, there is no need to come into contact with the stools 400 or even with the element of the article that has come into contact with the stools 400. Furthermore, when taking hold of the article 1 at two substantially diametral points of the inflatable tube 10, a good grip is obtained on the article 1 and any risk of accidental overturning is limited. Finally, since the stools 400 are trapped in the bottom compartment 20A, the risk of accidental contact between the stools 400 and some other surface, some other equipment, or the ground is more limited than with a diaper.

Second Embodiment

There follows a description of the second embodiment, concentrating on its differences with the first embodiment.

Thus, in the figures relating to the second embodiment and in the description below, elements of the second embodiment that are identical to elements of the first embodiment are referenced by the same reference numbers, and are mentioned again only when that is necessary.

Elements of the second embodiment that differ from the first embodiment are designated by reference numbers that are greater than 100.

Figure 5:
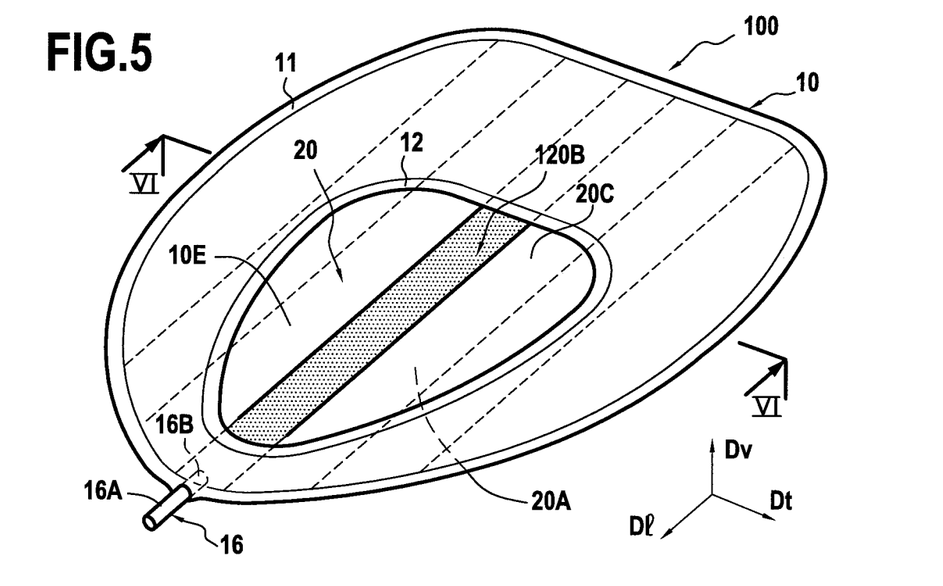
FIG. 5 is a perspective view from above of the article in a second embodiment of the invention.

FIG. 5 is a perspective view from above of the article 100 in the second embodiment. The article 100 is generally similar to the above-described article 1, except concerning the wall element.

Figure 6:
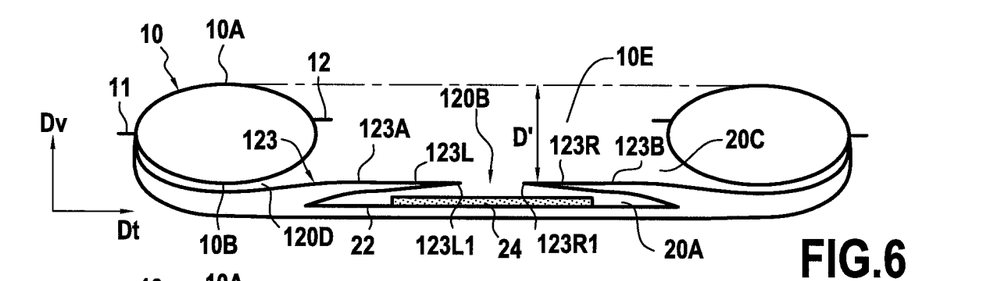
FIG. 6 is a section view on VI-VI of article shown in FIG. 5.

More precisely, and as can be seen better in FIG. 6, the article has an internal wall element 123 that corresponds to the internal wall element 23 of the first embodiment and like it that comprises at least one portion of flexible film. Once more, two flexible film portions 123A and 123B are shown, it being understood that the description below can be generalized to any number of flexible film portions.

In this embodiment, the respective top ends of the flexible film portions 123A and 123B are fastened to the outer connection edge 11 and not to the inner connection edge 12 or anywhere else on the bottom surface 10B of the inflatable tube 10. Once more, there is no need for the top ends of the flexible film portions 123A and 123B to be connected to the inflatable tube 10 in symmetrical manner. For example, if necessary, one of the two connections may be made via the outer connection edge 12 and the other may be made via the inner connection edge 11 or elsewhere on the bottom surface 10B.

Consequently, the obstacle formed to passing stools 400 is slightly lower than in the first embodiment.

As in the first embodiment, while the internal wall element is in its first configuration, the chamber 20 is subdivided into a top compartment 20C and a bottom compartment 20A that communicates with each other via an opening 120B.

Since the flexible film portions 123A and 123B are fastened via their top ends to the outer connection edge 11, a peripheral portion 120D of the top compartment 20C extends under the support surface 10A. If it is desired to further increase the capacity of the chamber 20, it is also possible to provide for a portion of the bottom compartment 20A to extend under the support surface 10A.

As in the example corresponding to the first embodiment, the flexible film portions 123A and 123B are folded so that each of them has a reentrant fold, given respective references 123L and 123R. The hinges 123L1 and 123R1 of these reentrant folds define the opening 120B, which is substantially slot-shaped.

Figure 8A:
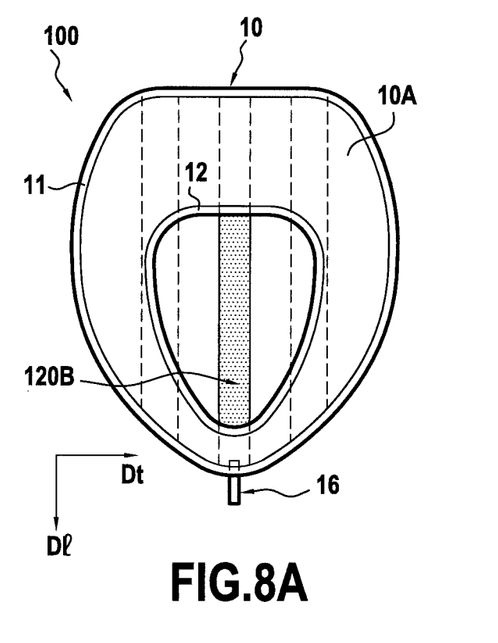
FIG. 8A is a plan view of the article shown in FIG. 5.
Figure 8B:
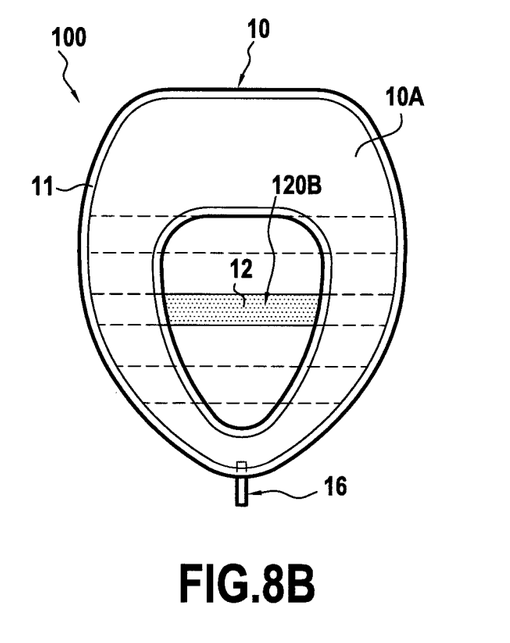
FIG. 8B is a view analogous to FIG. 8A, for a variant embodiment.

As can be seen in FIGS. 8A and 8B, the slot may be substantially in alignment with the longitudinal direction Dl, or substantially in alignment with the transverse direction Dt. The article operates identically in both circumstances.

In this second embodiment, and contrary to the first embodiment, the opening 120B is not closed in the vicinity of the inner connection edge 12, and on the contrary it extends under the support surface 10A of the inflatable tube 10 (see FIGS. 8A and 8B).

It should also be observed at this point that in order to simplify constructing the article 1, provision may be made for the bottom portion 22 and the flexible film portions 123A and 123B to be made from a single flexible film that is suitably arranged and that is connected at its ends to the outer connection edge 12.

In order to enable practically all of the user's stools to pass through on passing from the first configuration to the second configuration, as described above, the slot may have a length lying in the range 10 cm to 60 cm. Nevertheless, in this embodiment, it is preferable for the length of the slot to lie in the range 40 cm to 60 cm.

In order to provide communication that enables urine 300 to pass without allowing stools 400 to pass, the slot 120B may have a width lying in the range 0.5 cm to 3 cm.

Preferably, in order to ensure that the size of the opening 10E is sufficient to substantially surround the user's genital region, so as to avoid other equipment such as a bed being soiled by urine or stools, the opening 10E is selected to that its long dimension is not less than 20 cm.

Figure 7A:
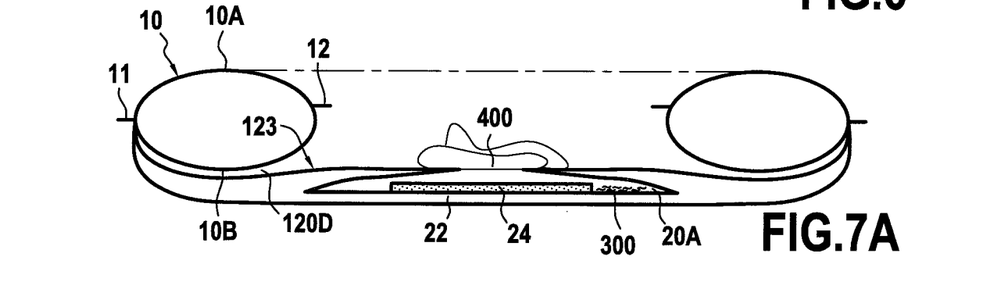
FIGS. 7A and 7B are section views on VI-VI of the article shown in FIG. 5, while it is in use.
Figure 7B:
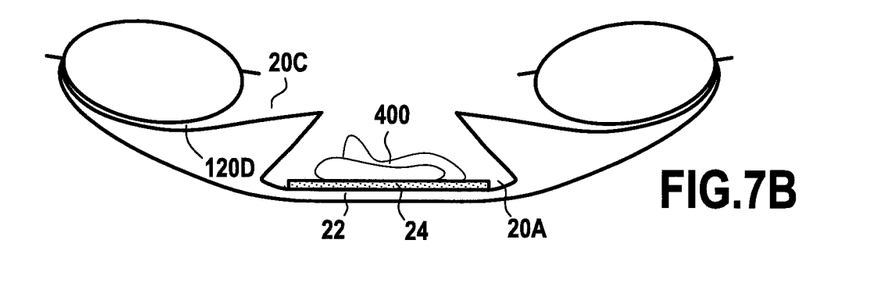

The operation of the article 100 is shown in FIGS. 7A and 7B and is identical to the operation of the first embodiment: when the article 100 is soiled by urine 300 and stools 400, the internal wall element 123 is caused to pass from its first configuration (FIG. 7A) to its second configuration (FIG. 7B) by taking hold of the inflatable tube 10 at two points of the inflatable tube 10, and then by lifting it upwards in the vertical direction Dv.

In the same manner as in the first embodiment, the reentrant folds 123L and 123R "unfold" progressively as the outer connection edge 11 is pulled upwards, the slot 120B widening progressively, with the obstacle formed by the reentrant folds 123L and 123R substantially disappearing, thereby enabling the stools 400 to pass towards the bottom 22 of the bottom compartment 20A. This obtains the same advantages in terms of hygiene as with the article 1 of the first embodiment.

In comparison with the article 1 of the first embodiment, the article 100 presents the following additional advantages.

In the first configuration of the internal wall element 123, the obstacle to passing stools 400 is slightly lower than in the first embodiment. For example, the distance D' between the internal wall element and the plane defined by the top of the support surface is of the order of 4 cm to 10 cm. This makes it possible to limit involuntary contact between the stools 400 and the skin of the user or the person replacing the article 100.

Furthermore, on passing from the first configuration to the second configuration, a slope is naturally created from the wall of the top compartment 20C towards the slot 120B. This contributes to causing the stools to pass towards the bottom compartment 20A. This makes the article 100 easier to use. In particular, compared with the first embodiment, there is less risk of the stools 400 becoming jammed in the top compartment 20C or on the inner connection edge 12.

Although the above articles 1 and 100 are described in a context where they are used by a bedridden user in an establishment such as a hospital or a retirement home, it is clear that the invention is not limited to this specific context. In particular, the article may also be used in a sitting position, and consequently it is not essential for the user to be prone on the article.

Although the present invention is described with reference to specific embodiments, it is clear that modifications and changes may be made to those embodiments without going beyond the general scope of the invention as defined by the claims. In addition, the individual characteristics of the various embodiments mentioned may be combined in additional embodiments. Consequently, the description and the drawings should be considered in a sense that is illustrative rather than restrictive.

The invention claimed is:

1. An article for collecting urine and stools of a user, the article comprising:
 a support surface for supporting buttocks of the user; and
 a chamber that communicates with an opening defined by the support surface and that presents a bottom portion; and
 a spacer for maintaining the bottom portion at a distance from the support surface;
 the chamber having an internal wall element that is situated at a position vertically intermediate between the support surface and the bottom portion and that is suitable for adopting a first configuration and a second configuration;
 wherein, in the first configuration, the internal wall element subdivides the chamber into a top compartment and a bottom compartment, and forms an obstacle between these compartments that is suitable for retaining stools in the top compartment while putting the compartments into communication for urine, and wherein, in the second configuration, the obstacle is substantially eliminated so as to allow stools to pass into the bottom of the chamber; and wherein in the first configuration, communication between the bottom and top compartments comprises an opening that is substantially slot-shaped, a slot being defined by hinges formed in two reentrant folds in two flexible film portions placed facing each other, wherein said obstacle is formed by said two reentrant folds and the two flexible film portions are connected at top ends of said flexible film portions to the support surface and at bottom ends of said flexible film portions to the bottom portion, such that passing of the internal wall element from the first configuration to the second configuration may be caused by pulling the support surface upwards in a vertical direction of the article wherein said reentrant folds progressively unfold thereby increasing a width of said slot and permitting said stools to pass through said slot towards said bottom portion.

2. An article as claimed in claim 1, wherein the internal wall element comprises at least one portion of flexible film.

3. An article as claimed in claim 2, wherein the obstacle is formed by at least one reentrant fold in at least one portion of flexible film.

4. An article as claimed in claim 1, wherein the slot lies substantially in one of a longitudinal direction of the article, and a transverse direction of the article.

5. An article as claimed in claim 4, wherein, in the first configuration, the width of the slot lies in the range 0.5 cm to 3 cm.

6. An article as claimed in claim 4, wherein the length of the slot lies in that range 10 cm to 60 cm.

7. An article as claimed in claim 1, wherein the bottom portion and the at least one portion of flexible film are formed out of the same piece of flexible film.

8. An article as claimed in claim 1, wherein the at least one portion of flexible film is connected at its top end to the support surface and at its bottom end to the bottom portion.

9. An article as claimed in claim 1, wherein a portion of the chamber extends under the support surface.

10. An article as claimed in claim 1, wherein an absorbent element is placed on the bottom portion.

11. An article as claimed in claim 1, wherein the spacer comprises an inflatable tube.

12. An article as claimed in claim 11, wherein the support surface is a top surface of an inflatable tube.

13. An article as claimed in claim 11, wherein the inflatable tube includes an inflation valve having a check valve.

14. An article as claimed in claim 1, wherein the long dimension of the opening defined by the support surface is not less than 20 cm.

* * * * *